United States Patent
Biewer et al.

(10) Patent No.: US 11,342,073 B2
(45) Date of Patent: May 24, 2022

(54) TRANSMITTED DISPLAY CASTING FOR MEDICAL DEVICES

(71) Applicant: Fresenius Medical Care Holdings, Inc., Waltham, MA (US)

(72) Inventors: John A. Biewer, Waltham, MA (US); Gurpreet Singh, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 424 days.

(21) Appl. No.: 15/719,885

(22) Filed: Sep. 29, 2017

(65) Prior Publication Data

US 2019/0102521 A1    Apr. 4, 2019

(51) Int. Cl.
| | | |
|---|---|---|
| *G06F 3/14* | (2006.01) | |
| *G16H 40/67* | (2018.01) | |
| *G16H 80/00* | (2018.01) | |
| *G06F 13/42* | (2006.01) | |

(52) U.S. Cl.
CPC .......... *G16H 40/67* (2018.01); *G06F 3/1454* (2013.01); *G06F 13/4282* (2013.01); *G16H 80/00* (2018.01); *G06F 2211/005* (2013.01); *G06F 2213/0042* (2013.01)

(58) Field of Classification Search
None
See application file for complete search history.

(56) References Cited

U.S. PATENT DOCUMENTS

| | | |
|---|---|---|
| 5,987,519 A | 11/1999 | Peifer et al. |
| 6,591,085 B1 | 7/2003 | Grady |
| 7,525,289 B2 | 4/2009 | Janik et al. |
| 8,698,741 B1 | 4/2014 | Wang et al. |
| 8,905,959 B2 | 12/2014 | Basaglia |
| 9,015,334 B2 | 4/2015 | Harris |
| 9,112,849 B1 | 8/2015 | Werkelin Ahlin et al. |
| 9,131,260 B2 | 9/2015 | Klarke et al. |

(Continued)

OTHER PUBLICATIONS

International Search Report and Written Opinion in International Application No. PCT/US2018/051040, dated Dec. 20, 2018, 16 pages.

(Continued)

*Primary Examiner* — Amr A Awad
*Assistant Examiner* — Donna V Bocar
(74) *Attorney, Agent, or Firm* — Fish & Richardson P.C.

(57) ABSTRACT

Medical devices may have the ability to connect through a secure gateway to a network, including both local and external networks. According to the described system, a connection component of the medical device may include a wireless connection dongle system using a wireless adapter, such as a dongle, that is inserted into and/or otherwise coupled to the medical device and that transmits or casts information wirelessly, such as via real-time streaming, to a separate receiving display. The communication may be facilitated by another dongle inserted into and/or otherwise coupled to the receiving display that receives the casted display screen. This transmitted casting capability provides the ability to connect the medical device, such as a peritoneal dialysis machine, to other display devices to duplicate the screen of the medical device on one or more larger or more easily accessible displays via secure one-way communication.

5 Claims, 7 Drawing Sheets

(56) References Cited

U.S. PATENT DOCUMENTS

| | | | |
|---|---|---|---|
| 9,178,891 | B2 | 11/2015 | Wang et al. |
| 9,252,950 | B2 | 2/2016 | Caspi |
| 9,271,033 | B2 | 2/2016 | Arling et al. |
| 9,286,854 | B2 | 3/2016 | Klarke et al. |
| D776,162 | S | 1/2017 | Beck et al. |
| 9,549,324 | B2 | 1/2017 | Birtwhistle et al. |
| 9,635,111 | B2 | 4/2017 | Wang et al. |
| 9,756,428 | B1 | 9/2017 | Shayandeh et al. |
| 10,173,008 | B2 | 1/2019 | Simpson et al. |
| 2007/0185545 | A1 | 8/2007 | Duke |
| 2009/0306573 | A1 | 12/2009 | Gagner et al. |
| 2011/0006876 | A1 | 1/2011 | Moberg et al. |
| 2011/0023077 | A1* | 1/2011 | Simon .................... H04N 5/445 725/134 |
| 2013/0132848 | A1* | 5/2013 | Bhatt .................... G06F 9/542 715/733 |
| 2015/0121466 | A1* | 4/2015 | Brands .................... H04L 63/08 726/4 |
| 2015/0135239 | A1* | 5/2015 | Oh .................... H04N 21/43637 725/81 |
| 2016/0103650 | A1* | 4/2016 | Lim .................... H04N 21/43615 345/2.2 |
| 2016/0206800 | A1 | 7/2016 | Tanenbaum et al. |
| 2016/0239250 | A1* | 8/2016 | Kim .................... G06F 3/1454 |
| 2016/0261974 | A1 | 9/2016 | Arrizza |
| 2017/0004106 | A1* | 1/2017 | Joshua .................... G06F 11/2289 |
| 2017/0076069 | A1 | 3/2017 | Moissl et al. |
| 2017/0087290 | A1 | 3/2017 | Medina et al. |
| 2019/0079855 | A1* | 3/2019 | Dewitt .................... G06F 8/65 |

OTHER PUBLICATIONS

Kumar et al., "A comparative study of secure device pairing methods," Pervasive and Mobile Computing 5(6):734-749, Dec. 1, 2009.

* cited by examiner

TRANSMITTED DISPLAY CASTING FOR MEDICAL DEVICES

TECHNICAL FIELD

This application relates generally to systems and methods for medical device displays and more particularly to transmitted display casting for medical devices including dialysis machines.

BACKGROUND

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

Medical devices, particularly home dialysis machines, are becoming smaller, less intrusive and more portable. Making devices smaller, however, means that there is less screen area available for display on the displays of the medical devices. Patients, especially those who are home patients such as home PD patients, may be older and have diminished eyesight and, despite the other benefits of smaller home medical devices, such patients would benefit from additional, larger and/or more conveniently accessible display capacity.

Accordingly, it would be desirable to provide a system that addresses the above-noted concerns and other issues.

SUMMARY

According to the system described herein, a medical system includes a medical device having an originating display, a receiving display, and a transmitted display casting system that wirelessly transmits a screen of the originating display that is received at the receiving display via a one-way wireless communication channel. The medical device may be a dialysis machine.

In various implementations, the transmitted display casting system may include a wireless dongle coupled to the medical device that casts the screen of the originating display to the receiving display directly or via a display interface device coupled to the receiving display. The wireless dongle and the receiving display or the display interface device may be joined to a same wireless local area network. The transmitted display casting system may include a first wireless dongle coupled to the medical device that casts the screen of the originating display to a second wireless dongle coupled to the receiving display, the first wireless dongle being securely paired with the second wireless dongle. The transmitted display casting system may include a casting controller of the medical device paired with a wireless dongle coupled to the receiving display, wherein the casting controller includes a software application running on the medical device and a wireless communication component internal to the medical device that performs the casting of the screen of the originating display. The transmitted display casting system may use a wireless gateway device providing a local area network, and the wireless gateway device may be disposed in a same home as is disposed the medical device. The one-way wireless communication channel may be provided via local area network connection, such as a Bluetooth connection and/or a WiFi connection. Alternatively or additionally, the one-way wireless communication channel may be provided over the Internet via a network infrastructure. The receiving display may have a display screen that is larger than a display screen of the originating display.

According further to the system described herein, a transmitted display casting system for a medical device includes a wireless transmission component that casts an originating display screen of the medical device via a one-way wireless communication channel, a wireless receiving component that receives the originating display screen over the one-way wireless communication channel, and a communication pairing component that securely pairs the wireless transmission component and the wireless receiving component for casting the originating display screen securely over the one-way wireless communication channel. The medical device may be a dialysis machine.

In various implementations, the wireless transmission component may be a first universal serial bus (USB) dongle and the wireless receiving component may be a second USB dongle. The communication pairing component may include electronics and software distributed between the first USB dongle and the second USB dongle, wherein electronics and distributed software of the first USB dongle and the second USB dongle establishes the one-way communication channel between the first USB dongle and the second USB dongle. The communication pairing component may include a wireless gateway device providing a local area network, and the first USB dongle and the second USB dongle are joined to the local area network. The communication pairing component may include a component of a connected health system, wherein the wireless receiving component is disposed at a location remote from the medical device, and wherein the wireless transmission component casts the originating display screen of the medical device to the remote wireless receiving component via the one-way wireless communication channel through the connected health system. The one-way communication channel may be provided via a local area network connection, such as a Bluetooth connection and/or a WiFi connection. Alternatively or additionally, the one-way wireless communication channel may provided over the Internet via a network infrastructure to one or more receiving displays. The system may include a receiving display coupled to the wireless receiving component that receives the originating display screen from the wireless receiving component and displays a duplicate screen of the originating display screen.

BRIEF DESCRIPTION OF THE DRAWINGS

Embodiments and features of the system described herein are explained with reference to the several figures of the drawings, which are briefly described as follows.

DETAILED DESCRIPTION

Figure 1:
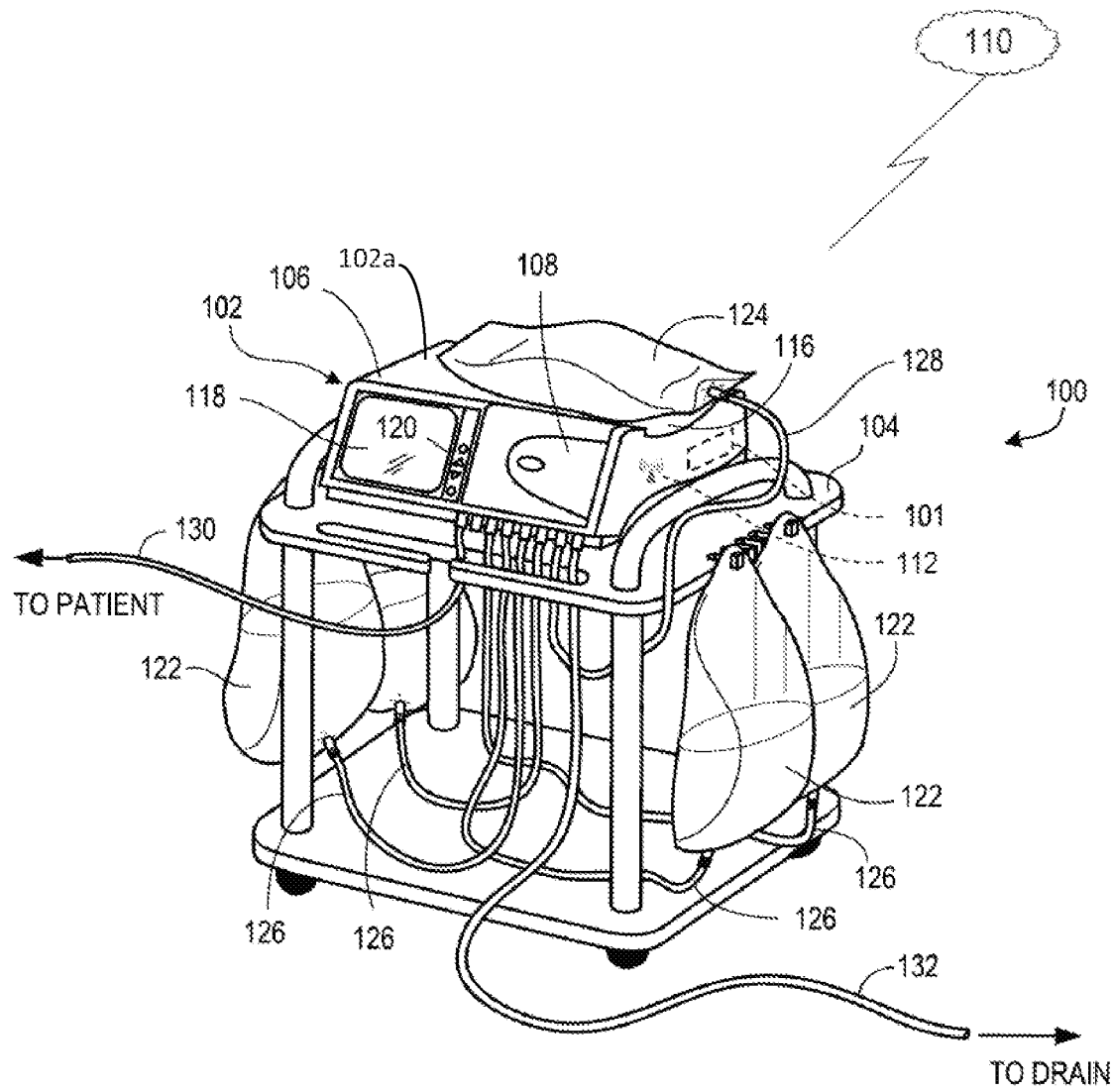
FIG. 1 illustrates an exemplary embodiment of a dialysis machine in a dialysis system configured in accordance with the present disclosure.

FIG. 1 shows an example of a medical device, implemented as a peritoneal dialysis (PD) system 100, that is configured in accordance with an exemplary embodiment of the system described herein. In some implementations, the PD system 100 may be configured for use at a patient's home (e.g., a home PD system). The PD system 100 may include a dialysis machine 102 (e.g. a PD machine, also referred to as a PD cycler) and in some embodiments may be seated on a cart 104. The dialysis machine 102 may include a housing 106, a door 108, and a cartridge interface for contacting a disposable PD cassette, or cartridge, when the cartridge is disposed within a compartment formed between the cartridge interface and the closed door 108. A heater tray 116 may be positioned on top of the housing 106. The heater tray 116 may be any size and shape to accommodate a bag of dialysate (e.g., a 5 L bag of dialysate). The dialysis machine 102 may also include a user interface such as a touch screen 118 and control panel 120 operable by a user (e.g., a caregiver or a patient) to allow, for example, set up, initiation, and/or termination of a PD treatment.

Dialysate bags 122 may be suspended from the sides of the cart 104, and a heater bag 124 may be positioned in the heater tray 116. Hanging the dialysate bags 122 may improve air management as any air is disposed by gravity to a top portion of the dialysate bag 122. Valves may be attached to a bottom portion of the dialysate bags 122 so fluid is drawn out and air delivery is minimized. Dialysate from the dialysate bags 122 may be transferred to the heater bag 124 in batches. For example, a batch of dialysate may be transferred from the dialysate bags 122 to the heater bag 124, where the dialysate is heated by the heating element. When the batch of dialysate has reached a predetermined temperature (e.g., approximately 98°-100° F., 37° C.), the batch of dialysate may be flowed into the patient. The dialysate bags 122 and the heater bag 124 may be connected to the cartridge via dialysate bag lines 126 and a heater bag line 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use.

The touch screen 118 and the control panel 120 may allow a user to input various treatment parameters to the dialysis machine 102 and to otherwise control the dialysis machine 102. In addition, the touch screen 118 may serve as a display. The touch screen 118 may function to provide information to the patient and the operator of the PD system 100. For example, the touch screen 118 may display information related to a dialysis treatment to be applied to the patient, including information related to a prescription.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., temperature and pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wired and/or wireless connection, as further discussed elsewhere herein. The dialysis machine 102 may include a connection component 112 configured to facilitate the connection to the network 110. The connection component 112 may be a transceiver for wireless connections and/or other signal processor for processing signals transmitted and received over a wired connection. Other medical devices (e.g., other dialysis machines) or components may be configured to connect to the network 110 and communicate with the dialysis machine 102. Although discussed herein principally in connection with a peritoneal dialysis machine, the system described herein may be used and implemented in connection with other types of medical devices having one or more displays, including home hemodialysis machines and/or other home medical devices.

Figure 2:
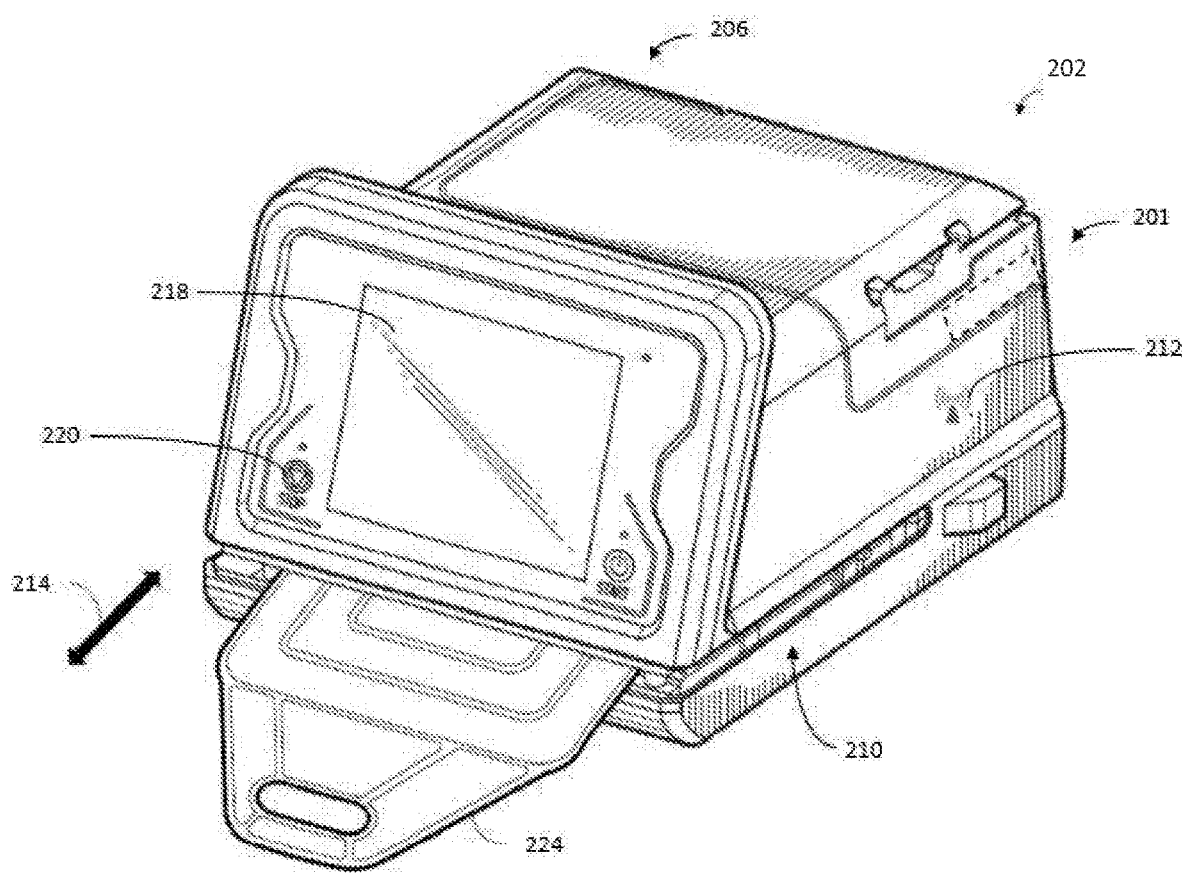
FIG. 2 illustrates another exemplary embodiment of a dialysis machine in accordance with the present disclosure.

FIG. 2 is a schematic illustration showing another exemplary embodiment of a dialysis machine 202 in accordance with the present disclosure. The dialysis machine 202 may be implemented in the peritoneal dialysis system 100 and may have at least some similar components as that of the dialysis machine 102, for example, including a housing 206, a processing module 201, a connection component 212, a touch screen 218, and a control panel 220 operable by a user (e.g., a caregiver or a patient) to allow, for example, set up, initiation, and/or termination of a PD treatment. The processing module 201 and the connection component 212 may be configured similarly to the processing module 101 and connection component 112 described above. However, instead of a heater tray being positioned on a top surface 102a of the housing as shown in FIG. 1 for the dialysis machine 102, one or more heating elements may be disposed internal to the machine 202. For example, a warmer pouch 224 may be insertable into an opening 210 in a direction indicated at arrow 214. In embodiments, the warmer pouch 224 may be configured so dialysate may continually flow through the warmer pouch (instead of transferred in batches) to achieve a predetermined temperature before flowing into the patient.

Medical devices may have the ability to connect through a secure Internet gateway to connect to a network, including a network outside the home to send and receive information to a clinic. The connection, network and data transmissions among components, both local and external, may be controlled and/other otherwise incorporated into a system that facilitates such functions with appropriate network infrastructure, and which may, in some implementations, be referred to as a connected health system. For further descriptions of systems for securely connecting, pairing and/or monitoring medical devices, such as in a connected health system, reference is made to US Pub. No. 20160206800 entitled "Remote Monitoring Interface Device and Mobile Application for Medical Devices" to Tanenbaum et al., US Pub. No. 20160261974 entitled "Associating Dialysis Accessories Using Near Field Communication" to Arrizza, US Pub. No. 20170087290 entitled "Short-Range Wireless Communication for a Dialysis System" to Medina et al., US Pub. No. 20170076069 entitled "Secure Network-Based System for Communication of Clinical Data" to Moissl et al., and U.S. Pat. No. 9,178,891 entitled "Remote Control of Dialysis Machines" to Wang et al., the disclosures of all of which are hereby incorporated by reference.

Figure 3:
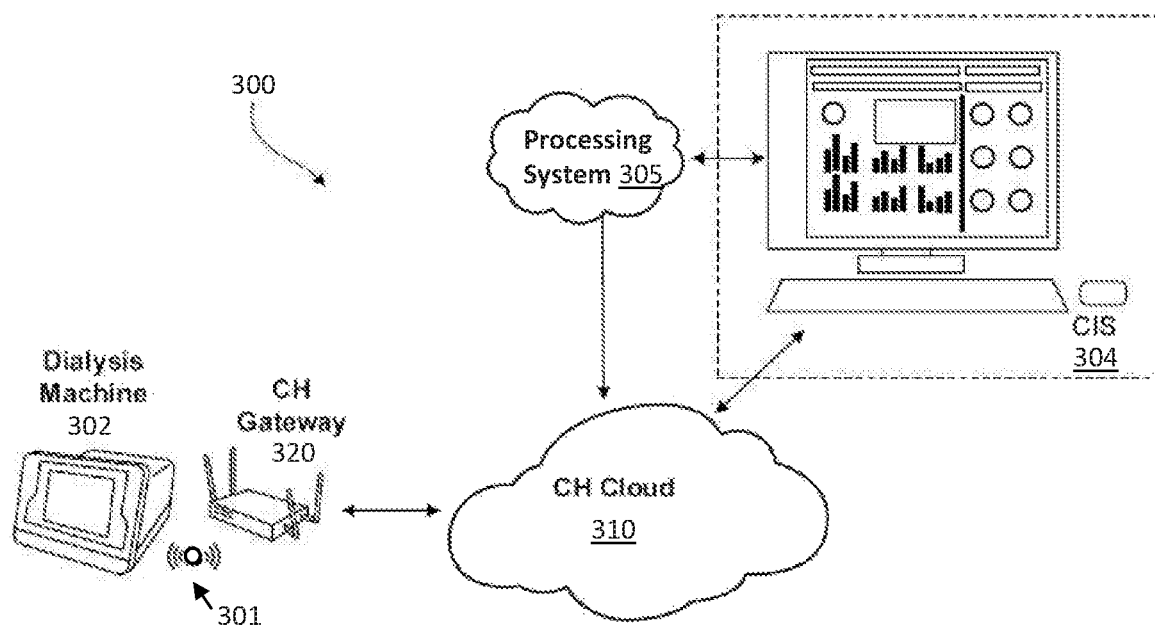
FIG. 3 is a schematic illustration showing an example of a connected health (CH) system that can include, among other things, a processing system, a CH cloud service and a CH gateway that may be used in connection with the system described herein.

FIG. 3 is a schematic illustration showing an example of a connected health (CH) system 300 that can include, among other things, a processing system 305, a CH cloud service 310 and a CH gateway 320 that may be used in connection with the system described herein. The processing system 305 may be a server or cloud-based system that processes, compatibility checks and/or formats medical information, including prescription information generated at a clinical information system (CIS) 304 of a clinic or hospital, in connection with data transmission operations of the CH system. The CH system may include appropriate encryption and data security mechanisms. The CH cloud service 310 may be a cloud-based application that serves as a communication pipeline (e.g., facilitates the transfer of data) among components of the CH system 300 via connections to a network such as the Internet (shown schematically with arrows). The CH Gateway 320 may serve as a communication device among components of the CH system 300. The CH gateway 320 is in communication with the dialysis machine 302 via a wireless connection 301, such as a Bluetooth, WiFi and/or other appropriate type of local wireless connection. The dialysis machine 302 may be similar to one or more of the dialysis machines 102, 202 discussed elsewhere herein. The CH gateway 320 is also in connection with the CH cloud service 310 via a secure network (e.g. Internet) connection. The CH gateway 320 is configured to transmit/receive data to/from the CH cloud service 310 and transmit/receive data to/from the dialysis machine 302. The dialysis machine 302 may poll the CH cloud service 310 for available files (e.g., via the CH gateway 320), and the dialysis machine 302 may temporarily store available files for processing.

In some implementations, the connection component of the dialysis machine may include use of a wireless connection system made using one or more universal serial bus (USB) wireless adapters, or dongles, inserted into and/or otherwise coupled to the dialysis machine and/or a receiving display. The wireless connection dongle system may transmit or "cast" information wirelessly to a receiving machine or device, such as via real-time streaming. This transmitted casting provides the ability to connect the dialysis machine (or other appropriate medical device) to other display devices, such as other displays, tablets, televisions, projects etc., directly or to display interface devices which then connect to the display device. In an implementation, the transmitting casting connection between the dialysis machine and the receiving display is a one-way communication only in which the receiving display receives information only from the dialysis machine. The display devices could also be one or more virtual displays. In some implementations, the transmitting casting of display information from the dialysis machine to another receiving display; in some instances, this may be referred as DialyCast. This transmitted casting may be a one-way connection from the dialysis machine to a receiving display. In some implementations, the connection may be directly between wireless transmission components internal to or inserted into the dialysis machine and the receiving display whereas, in other implementations, the connection may be made or facilitated via a secure gateway device, like the CH gateway device 320 discussed elsewhere herein.

Figure 4A:
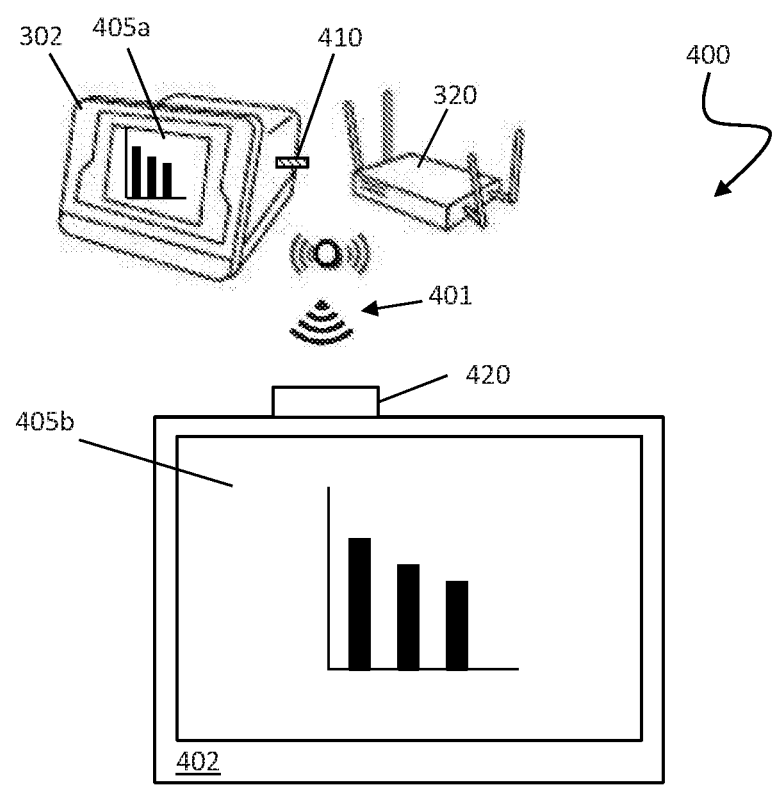
FIGS. 4A-4C are schematic illustrations showing example implementations of a transmitted display casting system in connection with the system described herein.
Figure 4B:
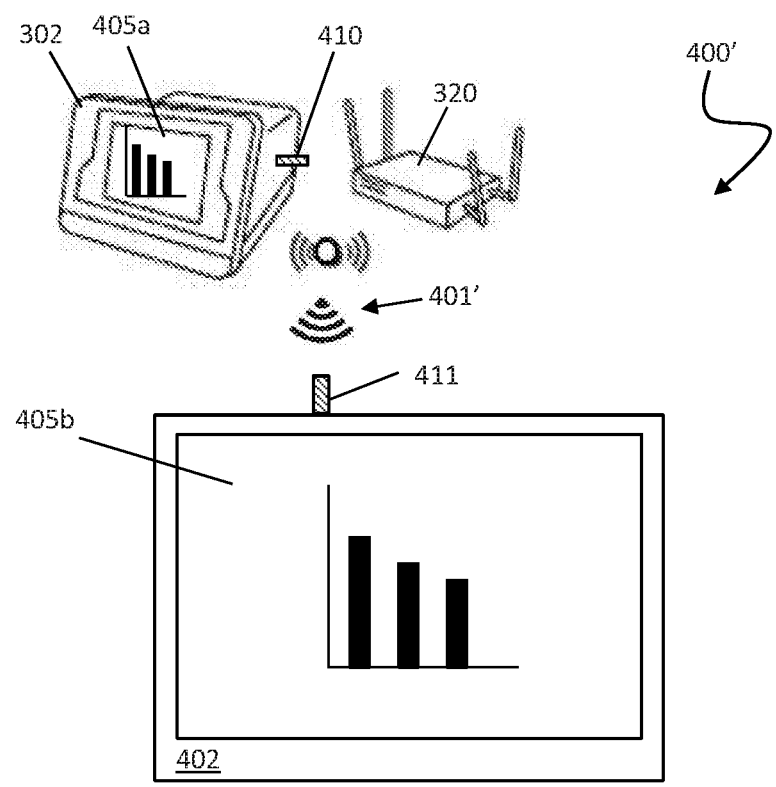
Figure 4C:
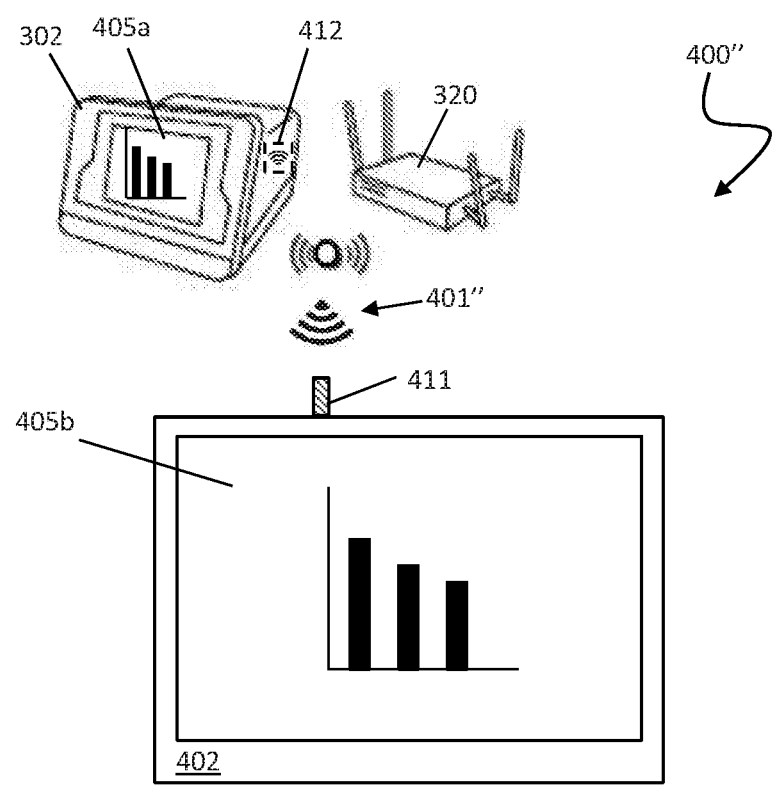

FIGS. 4A-4C are schematic illustrations showing example implementations and processing of a transmitted display casting system in connection with the system described herein.

FIG. 4A shows an example of a transmitted display casting system 400 for a medical device system according to an embodiment of the system described herein. The transmitted display casting system 400 may include components discussed elsewhere herein for a connected health system, including interfacing of the dialysis machine 302 and gateway 320 that may be disposed in a patient's home. A receiving display 402 is provided that may receive transmitted display casting from the dialysis machine 302 according to the system described herein. The receiving display 402 may be a separate display, TV, tablet, projector, smartphone etc. In the illustrated implementation, a USB dongle 410 is inserted into and/or otherwise coupled to the dialysis machine 302 that displays a screen 405a. The USB dongle 410 is securely paired (shown schematically as connection 401) either directly to the receiving display 402 and/or to a display interface device 420, e.g. digital interface devices such as Roku, AppleTV etc., which then connects to the receiving display 402. In an implementation, the pairing connection 401 is facilitated via the gateway 320 that may provide a local area network (LAN) enabling a Bluetooth, WiFi and/or other wireless local area connection between networked devices, e.g. networked devices joined to the same local area network. Via the paired connection of the USB dongle 410 and the receiving display 402/interface device 420, the screen 405a of the dialysis machine 302 is transmitted or cast in a one-way communication to the receiving display 402 which may display a duplicate screen 405b of the originating screen 405a. In this way, the receiving display 402 may enable a duplicate and/or larger size viewing of the screen 405a of the dialysis machine 302, which may enable easier or more accessible viewing for a patient or by others for training purposes, technical servicing etc., as more fully discussed elsewhere herein.

FIG. 4B shows another example of a transmitted display casting system 400' for a medical device system according to an embodiment of the system described herein. The transmitted display casting system 400' may be similar to the display casting system 400, except that, rather than a display interface device, a second USB dongle 411 is inserted into and/or otherwise coupled to the receiving display 402. The USB dongle 410 of the dialysis machine 302 and the USB dongle 411 of the receiving display 402 are securely paired (shown schematically via connection 401'). The multiple dongle system may benefit from enhanced security and encryption capabilities resulting in enhanced keying and pairing processes of the two (or more) dongles. The multiple dongle system may also offer beneficial ease-of-use, since the multiple dongles may be pre-configured to operate with each other and the appropriate medical devices and/or receiving displays to offer plug-and-play capabilities for the transmitted display casting features discussed herein. The USB dongle 410 casts the screen 405a of the dialysis machine 302 to the USB dongle 411 of the receiving display 402 and enabling the screen 405b, that is a duplicate of the screen 405a, to be displayed on the receiving display 402. As further discussed elsewhere herein, in some implementations, the USB dongle 410 and the USB dongle 411 may be in direct wireless communication with each other using antennas, electronics and software components of the respective dongles for performing the transmitted display casting, whereas, in other embodiments, the communication channel may be facilitated via a secure gateway device, such as the gateway 320 of the CH system.

FIG. 4C shows another example of a transmitted display casting system 400" for a medical device system according to an embodiment of the system described herein. The transmitted display casting system 400" is similar to the display casting system 400 and/or 400', except that, rather than a USB dongle inserted into the dialysis machine 302, the casting capabilities of the dialysis machine 302 is provided by an internal casting controller 412 that may incorporate the internal transmission components and/or capabilities of the dialysis machine 302 along with an application or other software component loaded onto the dialysis machine 302 that is directed to the function of casting the screen 405a of the dialysis machine 302, such as to an external USB dongle 411 inserted into the receiving display 402. Using the interface of the dialysis machine 302, a user may control pairing of the casting controller 412 with the USB dongle 411 to enable the casting capabilities to the USB dongle 411 for displaying the screen 405b on the receiving display 402 via a one-way communication channel (shown schematically via connection 401").

Figure 5:
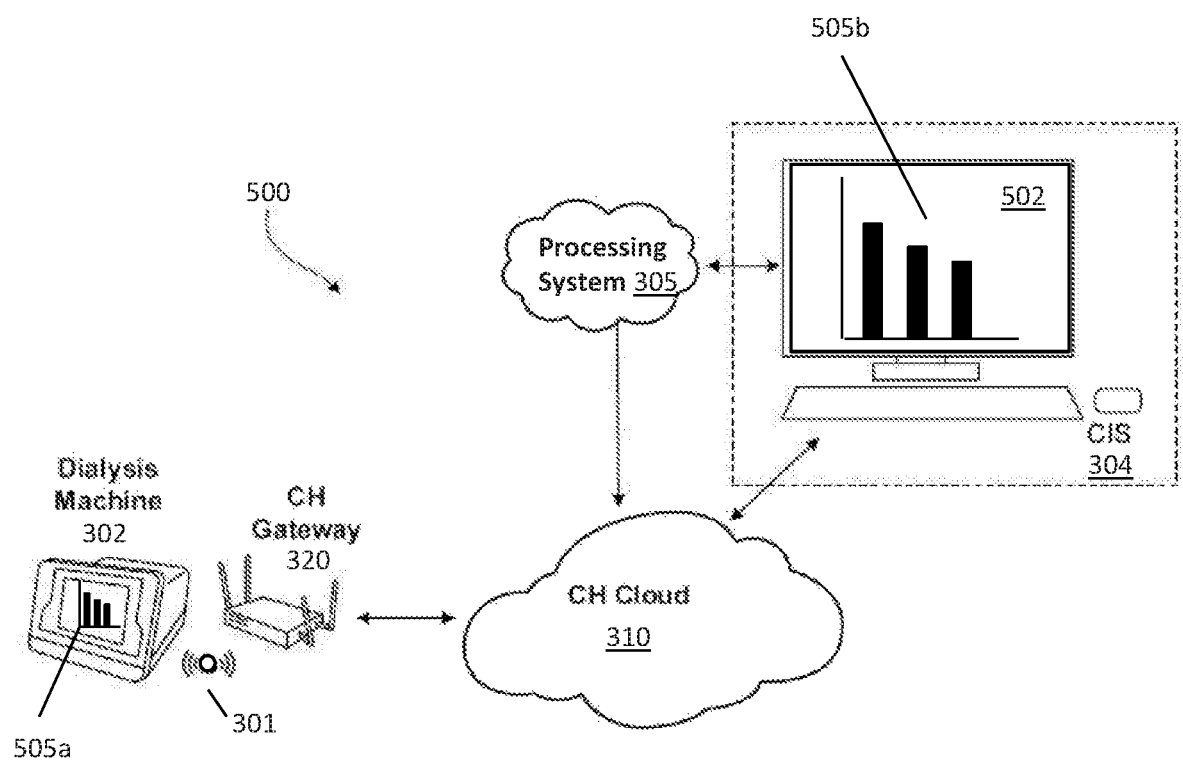
FIG. 5 is a schematic illustration showing another implementation of a transmitted display casting system in which the screen of the dialysis machine is cast remotely via components of the connected health system to an external display, such as a display of a the CIS at a clinic.

FIG. 5 is a schematic illustration showing another implementation of a transmitted display casting system 500 in which the screen of the dialysis machine 302 is cast remotely via components of the connected health system to an external, remote display 502, such as a display of the CIS 304 at a clinic and/or other remote location that performs technical or diagnostic servicing, for example. In this way, the transmitted display casting system 500 may provide for a remote monitoring system in which a clinician and/or technician may view a screen 505b that is a duplicate of a screen 505a at the dialysis machine 302. The casting may be performed over a network, such as the Internet, using the components of the connected health system, including the gateway 320 and CH Cloud 310, and which system may provide for appropriate and enhanced security and encryption capabilities.

Home use medical devices would benefit from the additional display capability of the transmitted display casting system according to the system described herein to give patients the ability to see and visualize information of a small display device on a larger screen that may already be in the home.

Another need addressed by the system described herein is training. Trying to train someone on a small touchscreen device may be difficult because hands may block a portion of the screen, and it may be hard to have multiple people around one small screen and still have good visibility. Having a duplicate display would enable the trainer to be at the device, and the trainee(s) to be in front of another larger display. The would be especially beneficial for training a group of nurses or other users at one time in a live format. Further, the system described herein could be extended to web meetings to allow a virtual retraining with a patient at home or large groups in different locations at the same time.

Yet another need that could be addressed by the system described herein is technical servicing. Especially with home use devices, when technical servicing is required or requested by a patient, a technician is often remote and cannot 'see' the medical device. With current medical devices the patient may call into a help line and the person on the other ends asks questions of the user to try to decipher where the patient is within the process (set-up, treatment, etc.) which usually entails instructing the user to describe the screen. The technician may also instruct the user to interact with the machine and then describe the results. This process is inefficient and can be frustrating. With a remote transmitted or casted display, the system described herein may enable the casting of the medical device display onto a secure web portal, initiated by the user, that may be remotely and securely accessed by an authorized technical service representative or other viewer. In particular, a benefit of this remotely casted display is that it is one-way, as opposed to the technician accessing the device through a remote desktop application and getting full access to the device. This limits the vulnerability to cyber-attacks and prevents someone from gaining access and control of the device remotely where they could access private patient information or change device settings.

Implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a memory card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

Embodiments and implementations of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A medical system, comprising:
a medical device having an originating display, the medical device being located in a home of a user;
a receiving display located in the home;
a transmitted display casting system that wirelessly transmits a screen of the originating display that is received at the receiving display via a one-way wireless communication channel, wherein the transmitted display casting system includes a first wireless dongle coupled to the medical device that casts the screen of the originating display to a second wireless dongle coupled to the receiving display via the one-way wireless communication channel, wherein the first wireless dongle is securely paired with the second wireless dongle, wherein the first wireless dongle and the second wireless dongle are pre-configured, prior to coupling the first wireless dongle to the medical device, to operate with each other and the medical device, wherein the receiving display displays a duplicate screen of the screen of the originating display, and wherein the transmitted display casting system prevents the receiving display from controlling or changing the originating display of the medical device; and
a gateway device located in the home that facilitates the one-way wireless communication channel between the first wireless dongle and the second wireless dongle via a local area network, the gateway device being configured to transmit data to or receive data from the medical device, and the gateway device being configured to communicate with an external network to transmit data to or receive data from the external network,
wherein the transmitted display casting system includes a communication pairing component, wherein the communication pairing component includes electronics and software distributed between the first wireless dongle and the second wireless dongle, and wherein the electronics and software establish the one-way communication channel between the first wireless dongle and the second wireless dongle via the gateway device.

2. The medical system of claim 1, wherein the medical device is a dialysis machine.

3. The medical system of claim 1, wherein the first wireless dongle and the second wireless dongle are joined to a same wireless local area network.

4. The medical system of claim 1, wherein the receiving display has a display screen that is larger than a display screen of the originating display.

5. The medical system of claim 1, wherein the first wireless dongle casts the screen of the originating display via real-time streaming to the second wireless dongle.

* * * * *

UNITED STATES PATENT AND TRADEMARK OFFICE
CERTIFICATE OF CORRECTION

PATENT NO. : 11,342,073 B2
APPLICATION NO. : 15/719885
DATED : May 24, 2022
INVENTOR(S) : John A. Biewer and Gurpreet Singh Page 1 of 1

It is certified that error appears in the above-identified patent and that said Letters Patent is hereby corrected as shown below:

In the Claims

Column 9, Lines 29-30, in Claim 1, delete "screen of the screen of the" and insert -- screen of the --.

Signed and Sealed this
Twenty-fourth Day of January, 2023

Katherine Kelly Vidal
*Director of the United States Patent and Trademark Office*